United States Patent
Guthrie et al.

(10) Patent No.: US 9,372,961 B1
(45) Date of Patent: Jun. 21, 2016

(54) PHARMACEUTICAL VERIFICATION CAMERA SYSTEM AND METHOD

(71) Applicant: Humana Inc., Louisville, KY (US)

(72) Inventors: Christopher Guthrie, Phoenix, AZ (US); Sean Guthrie, Phoenix, AZ (US); Michael Mahar, Phoenix, AZ (US); Atin Kapadia, Chandler, AZ (US)

(73) Assignee: Humana Inc., Louisville, KY (US)

( * ) Notice: Subject to any disclaimer, the term of this patent is extended or adjusted under 35 U.S.C. 154(b) by 471 days.

(21) Appl. No.: 13/960,709

(22) Filed: Aug. 6, 2013

Related U.S. Application Data (60) Provisional application No. 61/720,066, filed on Oct. 30, 2012.

(51) Int. Cl.
| | |
|---|---|
| *G06F 19/24* | (2011.01) |
| *G06F 19/00* | (2011.01) |
| *G01N 33/15* | (2006.01) |
| *H04N 5/232* | (2006.01) |

(52) U.S. Cl.
CPC ............ *G06F 19/3462* (2013.01); *G01N 33/15* (2013.01); *G06F 19/3468* (2013.01); *H04N 5/23216* (2013.01)

(58) Field of Classification Search
CPC .. H04N 9/735; H04N 5/23212; H04N 5/2351
USPC ........................................................ 700/245
See application file for complete search history.

(56) References Cited

U.S. PATENT DOCUMENTS

| | | | | |
|---|---|---|---|---|
| 7,697,834 B1* | 4/2010 | Tsai | ........................ | G02B 7/38 250/201.2 |
| 7,876,354 B1* | 1/2011 | Shapiro | .................. | H04N 5/232 348/180 |
| 2006/0259195 A1* | 11/2006 | Eliuk | ....................... | A61J 1/20 700/245 |
| 2014/0093174 A1* | 4/2014 | Zhang | ............... | G06F 17/30259 382/190 |

* cited by examiner

*Primary Examiner* — Sath V Perungavoor
*Assistant Examiner* — Clifford Hilaire
(74) *Attorney, Agent, or Firm* — Standley Law Group LLP (57) ABSTRACT

A pharmaceutical verification (PV) camera system that captures an image of the contents of a vial on an automated dispensing line is closed. Faster image processing time is achieved by utilizing a learning algorithm that stores camera parameters for a successful image associated with data for a prescription processed on the automated dispensing line. During processing of a prescription order, when the vial contents and availability of stored parameters is confirmed, the stored parameters are transmitted to the camera and an image of the vial contents is captured and stored. When a previously un-encountered or un-trained vial is detected, the camera engages the autofocus feature to capture an image. The learning algorithm evaluates the image based on feedback from one or more metric. Upon agreement with the metric standards, an image is accepted and archived and the camera parameters associated with that vial prescription are stored for later use.

14 Claims, 5 Drawing Sheets

PHARMACEUTICAL VERIFICATION CAMERA SYSTEM AND METHOD

CROSS-REFERENCE TO RELATED APPLICATIONS

This application claims priority to U.S. Provisional Patent Application Ser. No. 61/720,066, titled PHARMACIST VERIFICATION SYSTEM and filed Oct. 30, 2012, the content of which is incorporated herein by reference.

BACKGROUND

Many health benefit plan providers and retail pharmacies now offer their clients the option of obtaining prescription drugs by mail. Mail order pharmacies ship prescription drugs to a client's home so the client is not required to visit a pharmacy and to fill a prescription in person. For clients with chronic conditions or other conditions that require maintenance drugs, a mail order prescription program is an attractive benefit because it is more convenient for the clients and typically less expensive than obtaining prescription drugs at a neighborhood pharmacy. For many drugs, clients have the option of purchasing a drug fill in a 60-day or even a 90-day supply at a lower cost than a 30-day supply.

Many mail order pharmacies use automated systems and dispensing lines to process and ship a high volume of prescriptions on a daily basis. Depending upon how the technology is implemented and deployed within a mail order pharmacy, a substantial number of steps in the fulfillment process may be automated and the need for human intervention minimized. Mail order pharmacies operating in the US, like their neighborhood counterparts, must be licensed in a state and are subject to numerous rules and regulations established by the licensing state's board of pharmacy. One common requirement is that a pharmacy, whether a neighborhood pharmacy or a mail order pharmacy, must meet pharmacist verification for certain prescriptions. For automated mail order pharmacies, pharmacist verification is a manual step that must be integrated into the automated fulfillment process.

In many automated pharmacy systems, pharmaceutical verification is performed by capturing and displaying at a workstation the verification data that the pharmacist needs to review and verify a prescription order. The verification data typically includes prescribed drug data from the order (e.g., drug name, strength, dosage form, and quantity prescribed) and a digital image of a drug that has been dispensed into a vial for shipment to the patient. The digital images are typically acquired from one or more digital camera systems that are integrated into an automated dispensing line. The pharmacist reviews the prescription order data and image of the vial contents to confirm the proper drug has been added to the vial to be dispensed to the patient.

Although state boards of pharmacy typically do not require pharmacist verification for every prescription filled by a mail order pharmacy, the automated system must capture a digital image of every prescription that is filled so a record of the order and vial contents can be retrieved in the event questions about processing of the order arise. When pharmacist verification is required, the digital image of the vial contents along with the prescription order data allows the pharmacist to confirm the proper drug has been dispensed. Therefore, it is important for the mail order pharmacy to incorporate an image capture process into the automated prescription dispensing line.

A pharmaceutical verification camera system is an important component of an automated prescription dispensing system but frequently such camera systems are also a bottleneck in the dispensing system. The capsules and pills that are dispensed vary in size, color, and shape, and therefore, require different camera settings to capture a clear image. Furthermore, the appearance of the capsules and pills within a vial can vary based on the volume of the drug added to the vial. To capture a clear image of every filled vial, automated dispensing systems typically rely on the camera's autofocus and automated color balancing features to determine the appropriate settings (e.g., focus, white balance, and exposure time) for the image capture.

The camera's automated features are part of an open-loop system that relies completely on internal routines to converge on and deliver an image. The time required to change the auto-settings as well as capture multiple images can take several seconds. A camera host computer typically waits for a period of time while the camera's embedded controller optimizes the image. At the end of this arbitrary period, the software assumes it has captured a valid image. The pass/fail result in this context is only based on the existence of the image. There are no quality checks in place to confirm an image of sufficient quality has been captured. The camera host saves the image to the archive and updates the control system so the vial may progress through the pharmacy, but the quality of the image is unknown.

In many systems, the vials are queued for image processing simply because the camera cannot keep up with the volume of vials that are processed by the system. Therefore, there is a need for an improved pharmaceutical verification camera system that reduces or eliminates bottlenecks in an automated dispensing system.

SUMMARY

The present disclosure describes an improved pharmaceutical verification (PV) camera system that captures an image of the contents of a vial on an automated dispensing line. Faster image processing time is achieved by utilizing a learning algorithm that stores camera parameters for a successful image associated with data for a prescription order processed on the automated dispensing line. The stored camera parameters are applied to later vials with the same configuration (e.g., drug and pill count). The camera system further employs a series of checks and balances to evaluate image quality. These checks and balances are important for both training the camera and also in maintaining image quality after the training phase.

In an example embodiment, the camera applies stored parameters when it encounters a vial with contents that have been subjected to the learning algorithm. When the vial contents and availability of stored parameters is confirmed, the stored parameters are transmitted to the camera and an image of the vial contents is captured and stored. When a previously un-encountered or un-trained vial is detected, the camera engages the autofocus feature of the camera. The autofocus function engages and the learning algorithm evaluates the image based on feedback from one or more metric. Upon agreement with the metric standards, an image is accepted and archived and the camera parameters associated with that vial prescription are stored for later use. When a similar vial prescription is encountered by the camera, the stored camera parameters are retrieved and relayed to the camera. The camera adjusts to these settings and captures a successful image without engaging the auto focus and other auto-setting features, thus saving image processing time and reducing the likelihood of bottlenecks.

DETAILED DESCRIPTION OF EXEMPLARY EMBODIMENT(S)

The disclosed pharmaceutical verification (PV) camera system and method captures images of vial contents on an automated dispensing line. The camera system is conveyor mounted and comprises an expert machine learning system and algorithm that stores camera parameters of a successful image associated with data for the prescription. The stored camera parameters are applied to later vials with the same prescription. The captured images are archived and used for reference during verification in addition to providing a record of the vial contents.

In an example embodiment, the algorithm:

Interprets unique prescription information about an incoming order;

Determines if the prescription has been previously imaged;

Activates the camera image capture function;

Continuously evaluates the image quality prior to photo record creation; and

Stores the associated parameters with the captured image for forthcoming vials with similar characteristics.

In an example embodiment, software that comprises a camera learning algorithm and other custom imaging processing functions is used to control a digital camera. In an example embodiment, the control software is implemented as a library of functions. One of skill in the art would understand that in addition to employing a library, the features and functionality of the disclosed camera control software could be implemented and/or integrated in a digital camera in a variety of ways, including incorporating the features and functionality into the camera's standard control software or providing it as an add-on.

In an example embodiment, the camera controller library provides functionality for a camera host interface that controls a conveyor-mounted camera used for vial imaging. The camera controller library comprises an employment capture process for processing of vials with "known" contents and a training capture process for processing of vials with "unknown" contents. In an example embodiment, the camera controller library uses prescription order information, specifically the National Drug Code-NDC and pill count, for a pre-imaging process that determines whether camera settings for the NDC/pill count combination have been set.

In an example embodiment, a camera host interface initiates imaging of a vial. When the vial enters a section of the automated dispensing line controlled by the camera host interface, it captures a puck containing the vial, images the vial contents, and releases the puck. The camera host interface reads an RFID tag for the vial and determines the prescription order data associated with the vial (e.g., NDC and pill count). The NDC and pill count information is passed to the camera controller library. If the parameters are known, the employment capture process is initiated. If the parameters are unknown, the training capture process is initiated.

In the training capture process, a plurality of images are captured and evaluated for conformance within specified tolerances. In an example embodiment, the training capture process captures and reviews the sharpness of multiple images. If the sharpness between images is within a specified tolerance, the image parameters are accepted and stored for subsequent use. If the image sharpness varies substantially between the images, the image parameters are not accepted and an exception handling process is invoked. One of skill in the art would understand that image quality may be measured using many well-known techniques. Improvements in image quality may be achieved by minimizing optical aberrations such as motion blur, focus blur, color clarity, and image sharpness and depth. In an example embodiment, image quality is measured in terms of "blur" such that a blur detection scheme based on wavelet transform may be used in the training capture process.[1]

Figure 1:
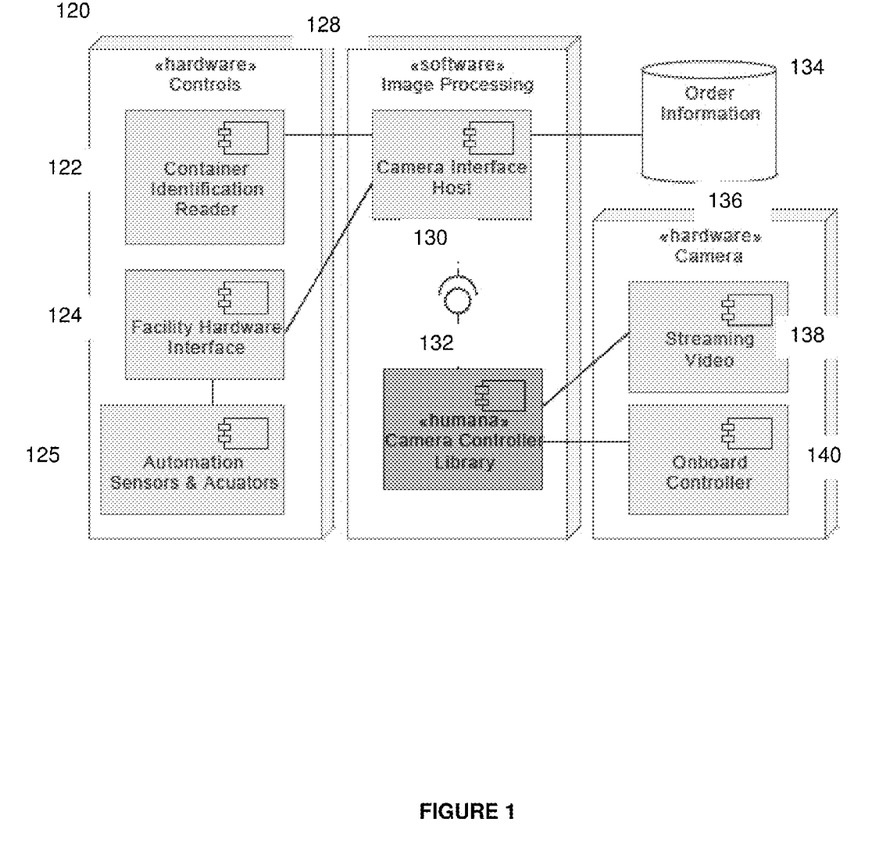
FIG. 1 is a camera system component diagram according to an example embodiment.

Referring to FIG. 1, a camera system component diagram according to an example embodiment is shown. The camera system comprises a plurality of hardware and software modules that interact to provide the disclosed features and functionality. The hardware controls comprise a container identification reader, facility hardware interface, and automation sensors and actuators. An image processing module comprises a camera host interface and camera controller library. The camera hardware comprises a streaming video component and onboard controller.

TABLE 1

Camera Components

| Module | Responsibility |
|---|---|
| Container Identification Reader (External to Camera) | Reading unique identification tag on vial carrier |
| Facility Hardware Interface (External to Camera) | Providing software with the state of the sensors<br>Providing software access to the actuators<br>Low-level processing |
| Automation Sensors & Actuators (External to Camera) | Monitor and manipulate the physical state of the pharmacy |
| Camera Interface Host (alt. Camera Host) | Interface with the pharmacy facility<br>Interface with the order information<br>Initiate image capture and finalize image capture<br>Acquire image from camera |
| Order Information | Database of all information for current orders |
| Streaming Video | Access to camera imaging sensor |
| On-board Controller | Access to camera sensor and lens configuration |
| Camera Controller Library | Interface to hardware and controller for image capture process |

The camera controller library provides unique functionality that substantially improves image capture quality and processing times. The camera host supplies the camera controller library with order information and a start signal. Control is then passed to the library until it completes processing and returns control to the camera host.

Figure 2:
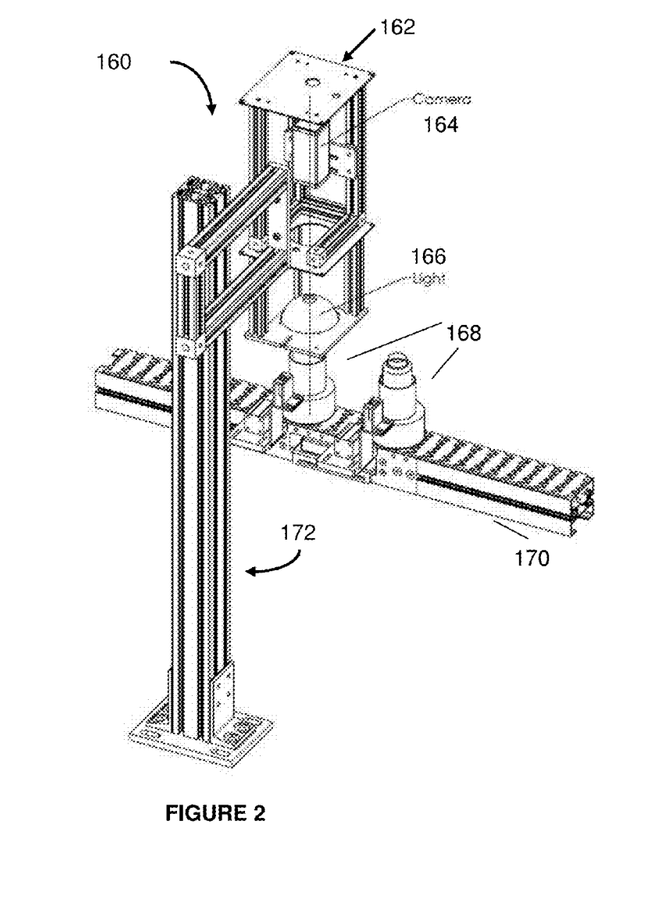
FIG. 2 is first in-line camera system assembly drawing according to an example embodiment.

Referring to FIG. 2, a first in-line camera assembly drawing according to an example embodiment is shown. The camera system assembly 160 comprises a support structure 172 and a camera mounting structure 162 to which the camera 164 is attached. A light 166 is engaged during the image capture phase to increase the quality of the images that are captured. The camera system assembly 160 is installed on an automated dispensing line and line control software interfaces with the camera host software to capture and store images of vials 168 that are transported on a conveyor of the automated dispensing line.

Figure 3:
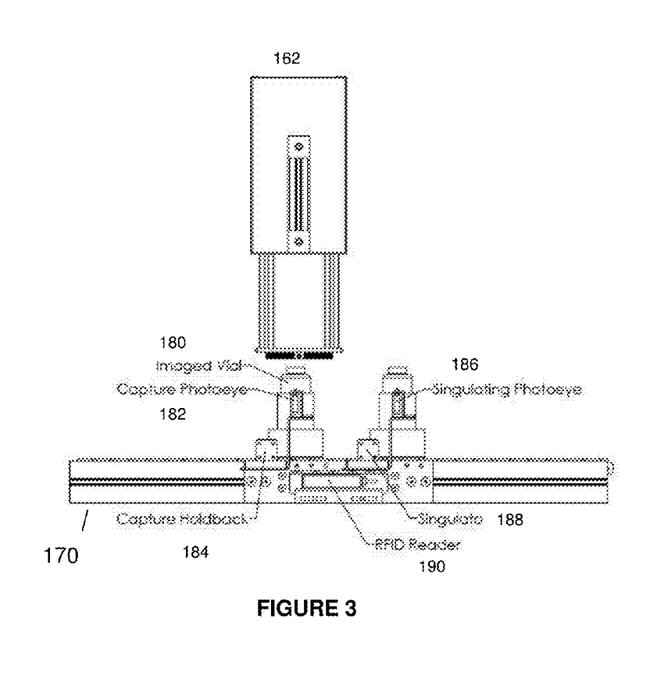
FIG. 3 is a second in-line camera system assembly drawing according to an example embodiment.

Referring to FIG. 3, a second in-line camera assembly drawing according to an example embodiment is shown. As vials travel on the conveyor 170, they are singulated 188 into an imaging position for image capture. In an example embodiment, a singulating photoeye 186 is used in the singulation process. Once a vial is singulated, it continues moving toward the camera system assembly. The RFID for the vial is read by the camera host interface using an RFID reader 190 integrated into the conveyor 170. A photoeye 182 and holdback 184 facilitate proper alignment of the vial for imaging and the camera controller library initiates a pre-imaging process to determine the vial contents based on the RFID. The RFID is used to retrieve prescription order data for the vial.

One of skill in the art would understand that other variables such as vial size, vial color, etc. that impact the possible vial configurations, and therefore, the sharpness and quality of each image, could be considered by the learning algorithm in determining camera parameters. The NDC and pill count values are transmitted to the camera controller library that then determines whether stored camera parameters for the NDC/pill count combination are available. If parameters for the NDC/pill count combination are available, they are communicated to the camera API 162 to capture an image of the vial 180 positioned under the camera. The image is captured and returned to the camera controller library which places the image in a repository for storage with the prescription order data. If parameters for the NDC/pill count combination are not available, the camera controller library invokes the training capture process.

Figure 4:
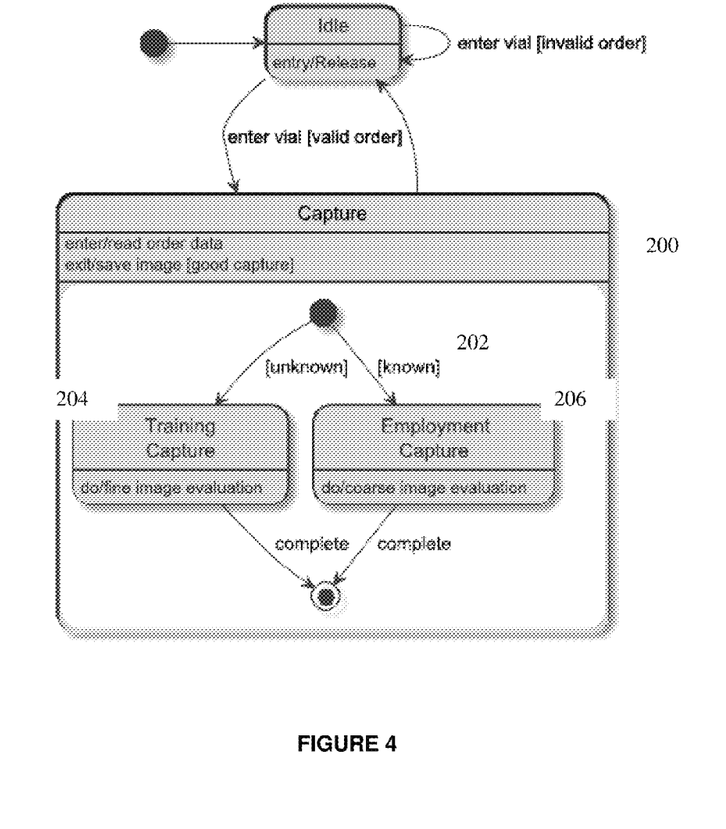
FIG. 4 is a software state diagram according to an example embodiment.

Referring to FIG. 4, a software state diagram according to an example embodiment is shown. When the camera system receives a vial, it reads the contents via the order information stored in a shared memory 200. The software categorizes the information into a binary value: known or unknown 202. An unknown configuration is a combination with which the software is unfamiliar. In this event, a training capture process 204 is spawned which is a slower, more rigorous capture process that acquires a valid image and parameters necessary to replicate that image. When the camera encounters a known configuration or can infer one using a heuristic method, it spawns an employment capture process 206. The employment capture process is much simpler and faster because the camera's parameters are known. It configures the camera and then captures the image. In an example embodiment, this frequently takes about ¹⁄₁₀th the time of the training capture.

Vial Capture Learning Algorithm

Camera parameters are functions of the pill type, quantity, and vial size. The learning algorithm borrows on concepts of artificial neural networks and logic, then discovers the functions through training. The implementation constantly evaluates and optimizes itself during captures to ensure the most optimal camera parameters are used. On a simple level, the training capture is a data update and the employment capture is a data look-up.

Training Evaluation

Figure 5:
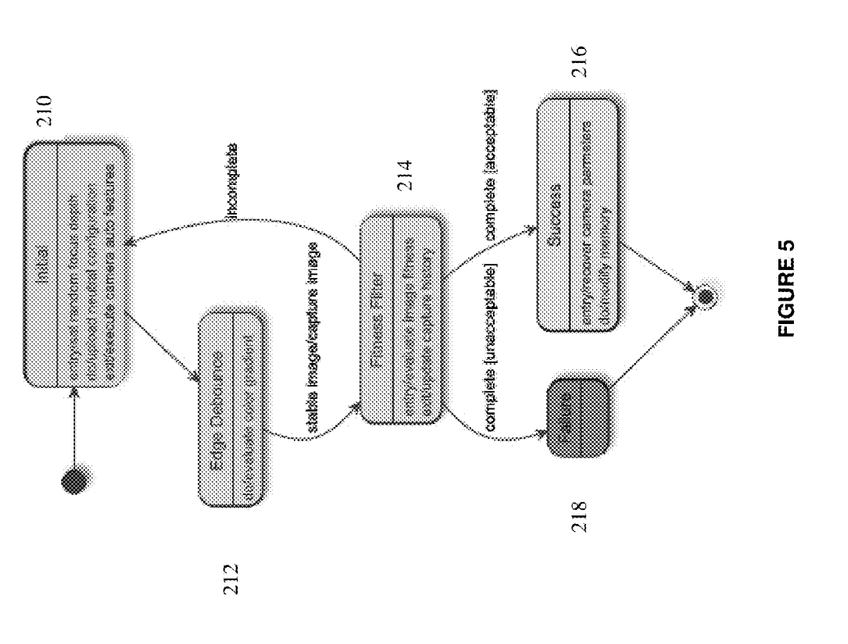
FIG. 5 is a training image evaluation state diagram according to an example embodiment.

Referring to FIG. 5, a training image evaluation state diagram according to an example embodiment is shown. To train the learning algorithm effectively, a high-quality image is used. The training process requires an image of sufficient quality because the machine learning system is live and unsupervised. The pharmaceutical aspect compounds the difficulties in training so the image filter must adapt to the constantly changing conditions that manifest themselves as pill size, shape, and color. Additionally, it must perceive image quality while avoiding false positives and negatives.

In an example embodiment, the training capture evaluation is a passive high-fidelity filter that acquires the best possible image from a live camera stream by evaluating the presented image only. The camera's internal routines are employed to find the best possible image. This approach results in a two-stage process:
1. Initialize the camera auto focus and color balancing and wait for it to converge on an image; and
2. Evaluate image for fitness and provide the control system with a go/no go signal.

Initial 210: The camera is initialized for a capture. This capture method is utilized when the camera's memory has no prior information on a vial configuration. The camera is configured to maximize the likelihood of convergence by setting the white balance and sensor gains to a neutral state. The focus depth is set to a random level within the vial. The random depth ensures that the numerical method employed by the embedded controller never starts with the same initial conditions, which makes multiple solution computational divergences unlikely. The final step in initialization starts the internal routines in the camera's embedded controller to auto focus and white balance.

Edge Debounce 212: In an example embodiment of the invention in which the camera controller is an open-controller, when the autofocus and/or color balancing routine are engaged, there is no direct feedback on finishing the routine. Therefore, the control loop is closed using the image stream. The edge debounce loop monitors the changing colors in the image and sends a stable image signal when the pixels have stopped changing with respect to time Fitness Filter 214: The fitness filter is an iterative evaluation that uses the relative consistency of captures to evaluate quality rather than an absolute tolerance. This method is more flexible and accurate when trying to evaluate the wide range of colors and shapes inherent in a pharmaceutical setting. Fitness is evaluated by a computationally intensive numerical method that measures the sharpness and clarity of the image. There are multiple, known strategies that may be employed for this evaluation. The filter evaluates the image and returns value within a range that varies from a sharp image to a swatch of one color. This value is utilized as a metric to evaluate the fitness of the image. Multiple images are evaluated and the deviation of these images is compared to a given tolerance. For example, the filter may determine that all images are within a percentage of one another. If the percentage is within the acceptable tolerance for a fit image it returns a successful capture 216, otherwise the capture fails 218.

Employment Evaluation

Figure 6:
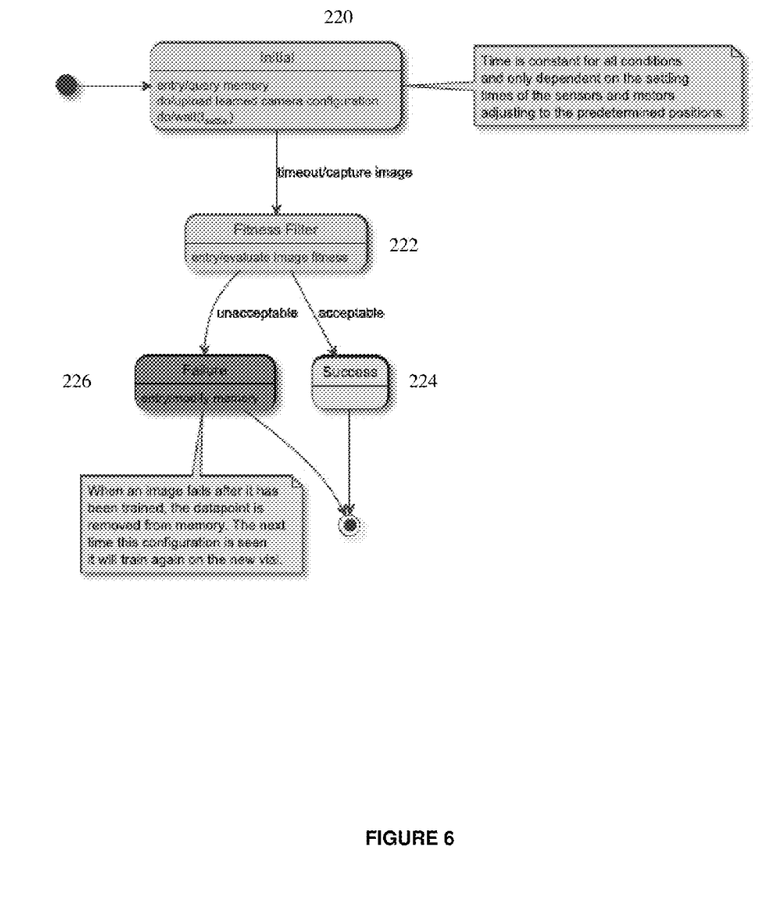
FIG. 6 is an image evaluation state diagram according to an example embodiment.

Referring to FIG. 6, an image evaluation state diagram according to an example embodiment is shown. In an example embodiment, the image evaluation is implemented as a fast passive heuristic filter that uses the previous training results as both an initial condition 220 as well as a tolerance for the vial configuration in the order. It uses the same intensive high-fidelity numerical method used in the training capture but with one pass 222. After the results are compared to previous captures, it either returns a successful 224 or failed signal 226. Upon a failed signal, it modifies the learning algorithm memory to take into account the invalid capture.

The disclosed PV camera system reduces image capture time for vials on an automated dispensing line by employing a learning algorithm to determine appropriate camera settings for various vial configurations. As vials are processed on the line, vial configuration data is used to determine whether camera settings have been established for the vial configurations. When a known vial configuration is encountered, the learned settings are retrieved from the library and applied to the camera for imaging of the vial contents. When an unknown vial configuration is encountered, a training capture process is invoked to learn the new configuration. When the previously unknown configuration is next encountered, the newly learned parameters may be applied.

While certain embodiments of the present invention are described in detail above, the scope of the invention is not to be considered limited by such disclosure, and modifications are possible without departing from the spirit of the invention as evidenced by the following claims:

REFERENCES

1. Tong, Hang-Hang, Hongjiang Zhang, and Changshui Zhang. "Blur Detection for Digital Images Using Wavelet Transform," 2004 IEEE International Conference on Multimedia and Expo, Vol. 1, pp. 17-20.

What is claimed is:

1. A computerized method for capturing an image of a drug vial on an automated dispensing line comprising:
   (a) prior to receiving an image of said drug vial from a camera, receiving at a computer expected vial configuration data for said drug vial;
   (b) receiving at said computer at least one camera setting associated with said vial configuration data;
   (c) transmitting from said computer to a camera on said automated dispensing line said at least one camera setting;
   (d) automatically configuring said camera according to said settings;
   (e) receiving at said computer from said camera an image captured using said at least one camera setting;
   (f) prior to receiving an image of a second drug vial from a camera, receiving at said computer vial configuration data for the second drug vial;
   (g) receiving at said computer an indicator said vial configuration data for said second drug vial is not associated with at least one camera setting;
   (h) invoking at said computer a camera learning algorithm to identify at least one camera setting associated with said vial configuration data for said second drug vial, said algorithm comprises causing the camera to:
      (1) focus a camera depth to a random level;
      (2) invoke an auto gain and an auto balancing feature;
      (3) wait for the image to achieve steady state with respect to color;
      (4) initialize an auto focus feature;
      (5) wait for the image to achieve steady state with respect to sharpness; and
      (6) capture a training image;
   (i) receiving at said computer from said camera learning algorithm at least one camera setting associated with said vial configuration data for said second drug vial; and
   (j) receiving at said computer from said camera a second image captured using said at least one camera setting associated with said vial configuration data for said second drug vial.

2. The computerized method of claim 1 wherein said vial configuration data comprises:
   a drug code and a pill count.

3. The computerized method of claim 1 wherein said at least one camera setting includes focus and optionally one or more of:
white red balance, white blue balance, gain, and exposure time.

4. The computerized system of claim 1 further comprising:
   (k) receiving at said computer said training image; and
   (l) evaluating at said computer image quality of training image for conformance within specified tolerances.

5. The computerized method of claim 4 further comprising:
   (m) storing at least one camera setting from said camera learning algorithm with said vial configuration data for said second drug vial.

6. The computerized method of claim 1 wherein receiving at a computer vial configuration data for said drug vial comprises:
   (1) receiving at said computer an identifier for said drug vial;
   (2) retrieving from a database using said identifier prescription order data for said drug vial; and
   (3) identifying at said computer in said prescription order data a drug code and a pill count.

7. A computerized system for capturing an image of a drug vial on an automated dispensing line comprising:
   (1) a line dispensing hardware controller that receives vial configuration data for said drug vial;
   (2) a camera host comprising a camera controller that:
      (a) receives said vial configuration data for said drug vial from said line dispensing hardware controller; and
      (b) identifies at least one camera setting associated with said vial configuration data;
      (c) receives vial configuration data for a second drug vial prior to receiving an image of a second drug vial from a camera;
      (d) receives an indicator said vial configuration data for said second drug vial is not associated with at least one camera setting;
      (e) invokes a train image process of a camera learning algorithm to identify at least one camera setting associated with said vial configuration data for said second drug vial, said train image process comprising causing the camera to:
         (i) focus a camera depth to a random level;
         (ii) invoke an auto gain and an auto balancing features;
         (iii) wait for the image to achieve steady state with respect to color;
         (iv) initialize an auto focus feature;
         (v) wait for the image to achieve steady state with respect to sharpness;
         (vi) capture a training image;
      (f) receives from said train image process at least one camera setting associated with said vial configuration data for said second drug vial; and
      (g) receives from said camera a second image captured using said at least one camera setting associated with said vial configuration data for said second drug vial;
   (3) a camera that:
      (a) receives from said camera host said at least one camera setting;
      (b) automatically configures itself according to said received setting(s); and
      (c) returns to said camera controller an image captured using said at least one camera setting.

8. The computerized system of claim 7 wherein said vial configuration data comprises a drug code and a pill count.

9. The computerized system of claim 7 wherein said at least one camera setting includes focus and optionally one or more of: white red balance, white blue balance, gain, and exposure time.

10. The computerized system of claim 7 where said camera controller further:
(1) receives said training image; and
(2) evaluates image quality of said training image for conformance within specified tolerances.

11. The computerized system of claim 10 wherein said camera controller stores said at least one camera setting from said train image process with said vial configuration data for said second drug vial.

12. A computerized method for capturing an image of a drug vial on an automated dispensing line comprising:
(a) storing in a database a plurality of vial configurations each consisting of a drug code and a pill count and each of which is associated with at least one camera setting;
(b) receiving at a camera controller a vial configuration for said drug vial;
(c) determining at said camera controller whether said vial configuration is in said database;
(d) in response to determining said vial configuration is in said database:
 (1) locating said at least one camera setting associated with said vial setting;
 (2) automatically configuring a camera using said camera settings; and
 (3) capturing an image of said drug vial using said at least one camera setting; and
(e) in response to determining said vial configuration is not in said database, invoking a training process to determine at least one new camera setting for said vial configuration, said training process comprises causing the camera to:
 (1) focus a camera depth to a random level;
 (2) invoke an auto gain and an auto balancing feature;
 (3) wait for the image to achieve steady state with respect to color;
 (4) initialize an auto focus feature;
 (5) wait for the image to achieve steady state with respect to sharpness; and
 (6) capture a training image.

13. The computerized method of claim 12 wherein said at least one camera setting includes focus and optionally one or more of: white red balance, white blue balance, gain, and exposure time.

14. The computerized method of claim 12 further comprising storing in said database said at least one new camera setting from said training process with said vial configuration.

* * * * *